United States Patent
Berndorfer

(10) Patent No.: US 6,508,100 B2
(45) Date of Patent: Jan. 21, 2003

(54) SYSTEM AND METHOD FOR RESETTING VEHICLE ENGINE OIL SENSORS

(75) Inventor: Axel H Berndorfer, El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/864,759

(22) Filed: May 24, 2001

(65) Prior Publication Data

US 2002/0174705 A1 Nov. 28, 2002

(51) Int. Cl.[7] .............................................. G01N 21/00

(52) U.S. Cl. ......................................................... 73/1.02

(58) Field of Search ................................ 73/1.02, 1.73; 702/100

(56) References Cited

U.S. PATENT DOCUMENTS

| | | | | |
|---|---|---|---|---|
| 4,706,193 A | * | 11/1987 | Imajo et al. ................. | 364/424 |
| 4,933,852 A | * | 6/1990 | Lemelson .............. | 364/424.03 |
| 6,208,245 B1 | * | 3/2001 | Post et al. ............... | 340/457.4 |
| 6,222,445 B1 | * | 4/2001 | Beckhusen .................. | 340/457 |
| 6,327,900 B1 | * | 12/2001 | McDonald et al. ........ | 73/117.3 |

FOREIGN PATENT DOCUMENTS

DE             101 20 015 A1  *  11/2001   ............ F01M/1/18

\* cited by examiner

*Primary Examiner*—Hezron Williams
*Assistant Examiner*—Charles D. Garber
(74) *Attorney, Agent, or Firm*—Margaret A. Dobrowitsky

(57) ABSTRACT

A method for resetting vehicle engine oil sensors includes determining whether a vehicle hood is opened. If the hood is opened, an oil sensor disposed in an oil pan is awakened and instructed to monitor the oil level. If, while the hood is opened, an oil parameter is altered a predetermined amount, the sensor and a corresponding output device are reset.

27 Claims, 1 Drawing Sheet

SYSTEM AND METHOD FOR RESETTING VEHICLE ENGINE OIL SENSORS

TECHNICAL FIELD

The present invention relates generally to engine oil sensors.

BACKGROUND OF THE INVENTION

Many modern motor vehicles are equipped with sensors that sense the level and/or condition of the vehicle engine oil. One type of oil level/condition sensor uses multiple electrodes that are immersed in the oil. The sensor electrically monitors the oil between the electrodes and sends signals representing the oil level to a microprocessor, e.g., vehicle onboard electronics. Moreover, the sensor monitors an oil parameter, e.g., the dielectric constant, conductivity, resistivity, or viscosity, that is indicative of the condition of the oil within the oil pan and sends signal to the microprocessor representing the oil condition.

Based on the signals from the sensor, a driver of a vehicle can be warned that the level has fallen below a critical level and fresh oil must be added to the system. On the other hand, the driver can be advised to change the oil, or add chemical additives to the oil, when the condition of the oil has deteriorated below a minimum threshold. Thus, the oil is changed as dictated by the actual condition of the oil and not by a predetermined arbitrary schedule.

The present invention recognizes that when the used oil is changed, or when fresh oil or an additive is added thereto, the oil level/condition sensor and corresponding warning indicators may need to be reset. One way to reset the sensor and warning indicators employs a complicated manual reset procedure. Another method includes using the sensor to periodically check for the presence of oil within the oil pan. If the sensor indicates that the oil pan is empty, and subsequently full, it is assumed that the oil has been changed and the sensor and corresponding warning indicators are reset.

Unfortunately, it happens that oil changes can occur very rapidly and the sensor can actually miss the oil change. On the other hand, the sensor may simply not sense the oil change because the oil does not drain away from the electrodes fast enough for the sensor to recognize that the oil pan is empty.

The present invention has recognized these prior art drawbacks, and has provided the below-disclosed solutions to one or more of the prior art deficiencies.

SUMMARY OF THE INVENTION

A method for resetting a vehicle engine oil sensor includes determining whether a switch that indicates when a vehicle is being serviced is opened and if so, alerting the sensor to wake. Preferably, while the sensor is awake, an oil parameter is monitored. If the oil parameter changes a predetermined amount, the sensor is reset. In a preferred embodiment, an engine oil level/condition output device is also reset.

In one aspect of the present invention, the oil parameter is an oil level. In another aspect of the present invention, the oil parameter is an oil condition parameter, e.g., an oil dielectric value, an oil conductivity, an oil resistivity, an oil permittivity, an oil viscosity, or an oil capacitance. The oil level/condition output device is, e.g., an add-oil indicator, a change oil indicator, an oil level indicator, or an oil condition indicator. Moreover, the switch is either a hood switch that indicates when a vehicle hood is opened or an oil fill tube switch that indicates when an oil fill tube is opened.

In yet another aspect of the present invention, a system for resetting an vehicle engine oil sensor includes a vehicle having an oil pan. An oil sensor is disposed in the oil pan such that it communicates with engine oil. Moreover, the vehicle includes a switch that indicates when the vehicle is being serviced. A microprocessor is connected to the oil sensor and the switch. In this aspect of the present invention, the microprocessor includes a program for determining when the switch is opened.

The present invention will now be described, by way of example, with reference to the accompanying drawings, in which:

DESCRIPTION OF AN EMBODIMENT OF THE INVENTION

Figure 1:
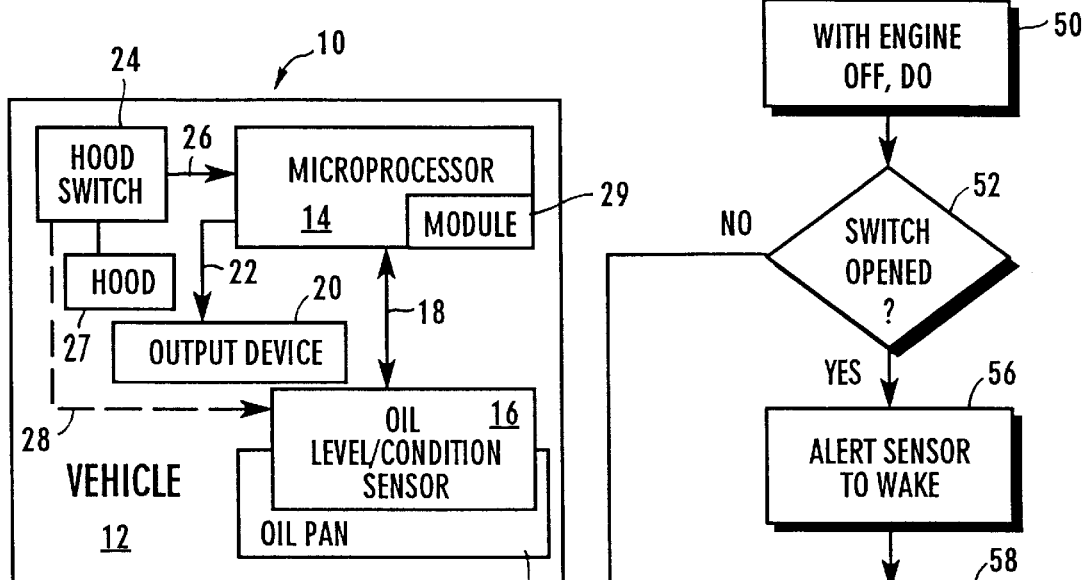
FIG. 1 is a block diagram of a system for resetting a vehicle engine oil sensor.

Referring initially to FIG. 1, a system for resetting a vehicle engine oil sensor is shown and generally designated 10. FIG. 1 shows that the system includes a vehicle 12 in which a microprocessor 14 is installed. It is to be appreciated that the microprocessor 14 can be an onboard chip such as, vehicle onboard electronics. Moreover, it is to be appreciated that the microprocessor 14 can be a chip within the sensor, described below.

As shown in FIG. 1, an oil level/condition sensor 16 is connected to the microprocessor 14 via electric line 18. The oil level/condition sensor 16 is installed in an oil pan 19 such that the level and/or condition of oil therein can be monitored. FIG. 1 shows an output device 20 that is connected to the microprocessor 14 via electric line 22. It is to be appreciated that the output device 20 can be an audible warning device, e.g., a buzzer or audible alarm. The output device 20 can also be a visual warning device, e.g., an add-oil indicator, or a change oil indicator. Moreover, it is to be appreciated that the output device 20 can be an oil level indicator that provides a visual display of the level of oil within the oil pan or an oil condition indicator that provides a visual display of the condition of the oil within the oil pan.

FIG. 1 also shows a hood switch 24 that is connected to the microprocessor 14 via electrical line 26. In a preferred embodiment, the hood switch 24 is mechanically coupled to a vehicle hood 27 and sends a signal to the microprocessor when the hood 27 is opened, e.g., to facilitate an oil change. It is to be appreciated that hood switch 24 may be connected directly to the sensor 16, as indicated by dashed line 28, and when the hood switch 24 is opened it can directly alert the sensor 16 to wake as described in detail below. It is to be appreciated that the hood switch 24 can be a non-contact device, e.g., one that employs a magnet and a magnetic field sensor. As shown in FIG. 1, the system further includes a control module 29 within the microprocessor 14.

Figure 2:
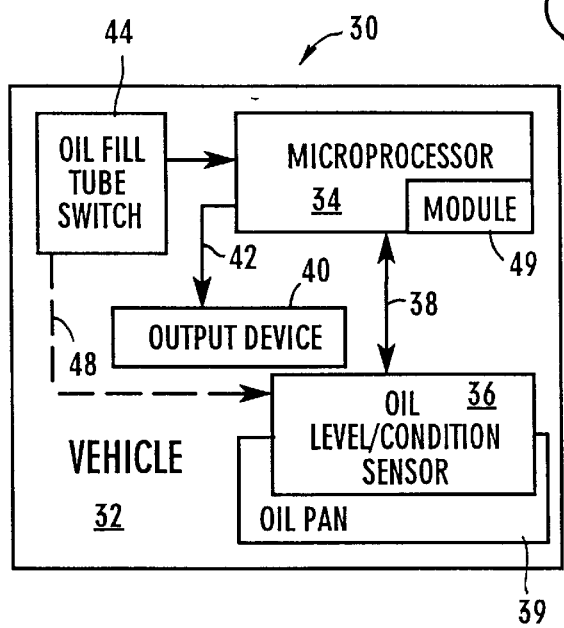
FIG. 2 is a block diagram of an alternate system for resetting a vehicle engine oil sensor.

Referring to FIG. 2, an alternate system for resetting a vehicle engine oil sensor is shown and generally designated 30. FIG. 2 shows that the system 30 includes a vehicle 32 in which a microprocessor 34 is installed. As shown in FIG. 2, an oil level/condition sensor 36 is connected to the microprocessor 34 via electric line 38. The oil level/condition sensor 36 is installed in an oil pan 39 such that the level and/or the condition of oil therein can be monitored. FIG. 1 shows an output device 40 that is connected to the microprocessor 34 via electric line 42.

FIG. 2 also shows a oil fill tube switch 44 that is connected to the microprocessor 34 via electrical line 46. The oil fill tube switch 44 is incorporated into an oil fill tube such that when the oil fill tube is opened, e.g., a cap is removed, a signal is sent to the microprocessor 34. It is to be appreciated that oil fill tube switch 44 may be connected directly to the sensor 36 as indicated by dashed line 48. As such, when the oil fill tube switch 44 is opened a signal can be sent directly from the switch 44 to the sensor 36 in order to alert the sensor 36 to wake as described below. As shown in FIG. 1, the system further includes a control module 49 within the microprocessor 34. It is to be appreciated that either of the above-described systems 10, 30 can be wireless. In other words, the switch 24, 44 can transmit a signal to the microprocessor 14, 34 or the sensor 16, 36 to indicate that the switch 24, 44 has been opened. Furthermore, the microprocessor 14, 34 can transmit a signal that is received by the output device 20, 40 when it is necessary to reset the output device 20, 40, as described below.

In either system 10, 30, the microprocessor 14, 34 includes a series of computer-executable instructions, as described below, which will allow the microprocessor 14, 34 to determine when the vehicle engine oil has been changed, or added to, and reset the oil level/condition sensor 16, 36 immediately thereafter. These instructions may reside, for example, in the module 29, 49 of the microprocessor 14, 34 which, when programmed with the present logic, establishes a computer program product.

Alternatively, the instructions may be contained on a data storage device with a computer readable medium, such as a computer diskette having a data storage medium holding computer program code elements. Or, the instructions may be stored on a DASD array, magnetic tape, conventional hard disk drive, electronic read-only memory, optical storage device, or other appropriate data storage device. In an illustrative embodiment of the invention, the computer-executable instructions may be lines of compiled C++ compatible code. As yet another equivalent alternative, the logic can be embedded in an application specific integrated circuit (ASIC) chip or other electronic circuitry.

Figure 3:
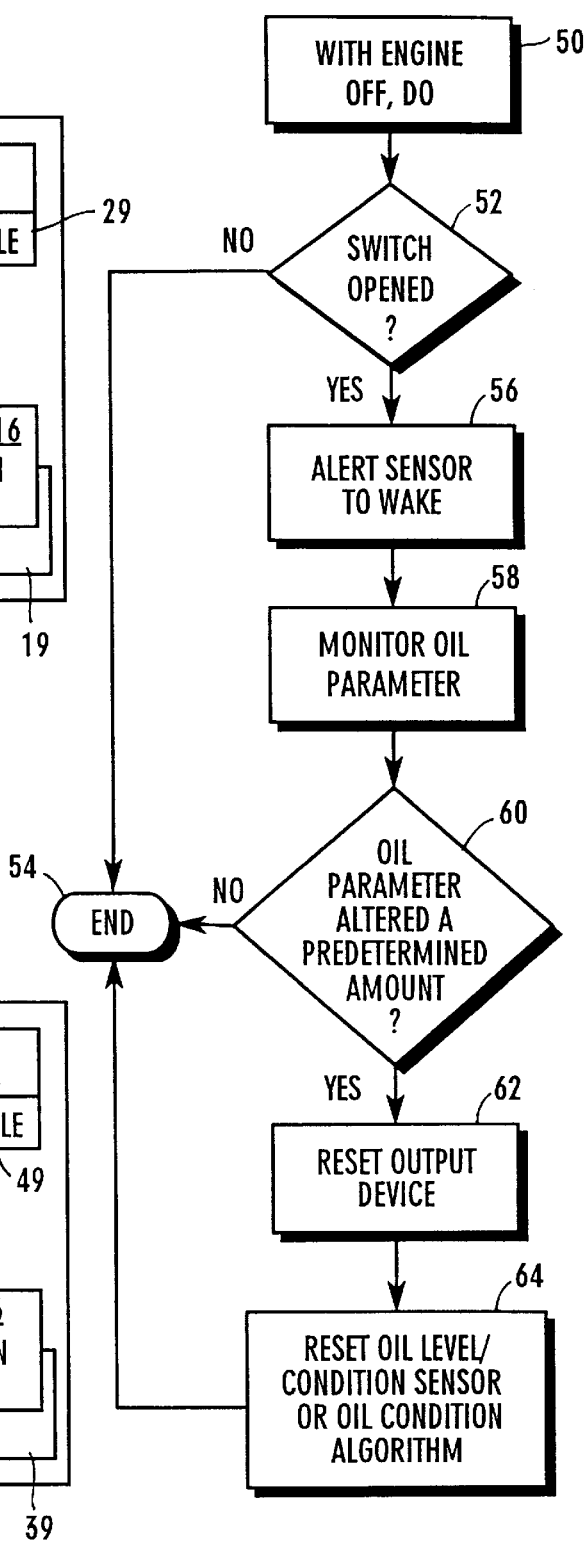
FIG. 3 is a flow chart of a method for resetting a vehicle engine oil sensor.

Referring to FIG. 3, the oil sensor reset logic is shown. Commencing at block 50, with the vehicle engine off, a do loop is entered wherein the succeeding steps are performed. Moving to decision diamond 52, it is determined whether the hood switch 24 or the oil fill tube switch 44 is opened. If not, the logic ends at state 54. If the hood switch 24 or the oil fill tube switch 44 is opened, the logic proceeds to block 56 where the oil sensor 16, 36 is alerted to wake. It is to be appreciated that the sensor 16, 36 remains awake for a predetermined time period or until another event occurs, e.g., the opened switch 24, 44 is closed. In the case of a sensor that cycles between a sleep mode and an awake mode, the frequency of the cycle is increased. Returning to the logic, at block 58, while the sensor 16, 36 is awake, an oil parameter is monitored.

Moving to decision diamond 60, it is determined whether an oil parameter is altered a predetermined amount. It is to be understood that the parameter can be the oil level or a parameter indicative of the oil condition, e.g., oil dielectric value, oil resistivity, oil conductivity, oil permittivity, oil viscosity, or capacitance. If the parameter has not been altered a predetermined amount, the logic ends at state 54. On the other hand, if the parameter has been altered a predetermined amount, indicating that the oil has been changed or a chemical additive or fresh oil has been added to the oil in the oil pan 19, 39, the logic continues to block 62 where the output device 20, 40, e.g., an add-oil indicator or critical oil condition indicator, is reset. Thereafter, at block 64, the oil level/condition sensor 16, 36 is reset. In the case of a system that uses an oil condition algorithm to mathematically determine the rate of decay of the oil condition based on factors such as the elapsed time that the oil has been used and the engine operating conditions, the oil condition algorithm is reset. Then, the logic ends at state 54.

With the configuration of structure and logic described above, it is to be appreciated that the system and method for resetting vehicle engine oil sensors can be used to relatively easily reset an engine oil sensor and a corresponding output device immediately following an oil change. Moreover, the sensor and output device can be reset after fresh oil or a chemical additive is added to the working oil.

While the particular SYSTEM AND METHOD FOR RESETTING VEHICLE ENGINE OIL SENSORS as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

I claim:

1. A method for resetting a vehicle engine oil sensor, comprising the acts of:
   determining whether a switch indicative of vehicle servicing is opened; and
   if so, alerting the sensor to wake for a predetermined time period.

2. The method of claim 1, further comprising the acts of:
   monitoring an oil parameter; and
   resetting the sensor at least partially based on the monitoring act.

3. The method of claim 2, further comprising the act of:
   resetting an oil level/condition output device.

4. The method of claim 1, wherein the sensor cycles between a sleep mode and an awake mode and the method further comprises the act of:
   if the switch is opened, increasing the frequency of the cycle.

5. The method of claim 1, further comprising the acts of:
monitoring an oil parameter; and
resetting an oil condition algorithm.

6. The method of claim 1, further comprising the act of:
determining whether the oil parameter has altered a predetermined amount; and
resetting the sensor at least partially based on thereon.

7. The method of claim 6, further comprising the act of:
resetting an oil level/condition output device.

8. The method of claim 7 wherein the oil level/condition output device is: an add-oil indicator, a change oil indicator, an oil level indicator, or an oil condition indicator.

9. The method of claim 6, wherein the oil parameter is an oil level.

10. The method of claim 6, wherein the oil parameter is an oil condition parameter.

11. The method of claim 10, wherein the oil condition parameter is: an oil dielectric value, an oil conductivity, an oil resistivity, an oil permittivity, an oil viscosity, or an oil capacitance.

12. The method of claim 1, wherein the switch is a hood switch that indicates when a vehicle hood is opened.

13. The method of claim 1, wherein the switch is an oil fill tube switch that indicates when an oil fill tube is opened.

14. A system for resetting a vehicle engine oil sensor comprising:
a vehicle and an oil pan;
an oil sensor disposed in the oil pan such that it communicates with engine oil;
a switch within the vehicle, the switch indicating when the vehicle is serviced; and
a microprocessor communicating with the oil sensor and the switch, the microprocessor including a program for determining when the switch is opened, the program including logic means for alerting the sensor to wake if the switch is opened.

15. The system of claim 14, wherein the program further comprises:
logic means for monitoring an oil parameter;
logic means for resetting the sensor at least partially in response to the monitoring logic means.

16. The system of claim 15, wherein the program further comprises:
logic means for resetting an engine oil level/condition output device.

17. The system of claim 14, wherein the program further comprises:
logic means for determining whether the oil parameter has altered a predetermined amount; and
logic means for resetting the sensor at least partially based on thereon.

18. The system of claim 17, wherein the program further comprises:
logic means for resetting an oil level/condition output device.

19. The system of claim 18, wherein the oil level/condition output device is: an add-oil indicator, a change oil indicator, an oil level indicator, or an oil condition indicator.

20. The system of claim 17, wherein the oil parameter is an oil level.

21. The system of claim 17, wherein the oil parameter is an oil condition parameter.

22. The system of claim 21, wherein the oil condition parameter is: an oil dielectric value, an oil conductivity, an oil resistivity, an oil permittivity, an oil viscosity, or an oil capacitance.

23. The system of claim 14, wherein the switch is a hood switch that indicates when a vehicle hood is opened.

24. The method of claim 14, wherein the switch is an oil fill tube switch that indicates when an oil fill tube is opened.

25. The system of claim 14, wherein the switch communicates directly with the sensor.

26. The system of claim 14, wherein the sensor cycles between a sleep mode and an awake mode and the program further includes:
logic means for increasing the frequency of the cycle if the switch is opened.

27. The system of claim 14, wherein the program further comprises:
logic means for monitoring an oil parameter; and
logic means for resetting an oil condition algorithm.

* * * * *